(12) United States Patent
Sauer et al.

(10) Patent No.: US 6,468,560 B2
(45) Date of Patent: Oct. 22, 2002

(54) CONTROLLED RELEASE DOSAGE FORM OF [R-(Z)]-α-(METHOXYIMINO)-α-(1-AZABICYCLO[2.2.2]OCT-3YL) ACETONITRILE MONOHYDROCHLORIDE

(75) Inventors: Joseph Peter Sauer, Sarasota, FL (US); Susan Marie Milosovich, Phoenixville, PA (US); William Thomas Muldoon, Philadelphia, PA (US); James Albert Napper, Pound Hill (GB); Laurence Rousseau, Broxbourne (GB)

(73) Assignees: SmithKline Beecham p.l.c., Brentford (GB); SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/956,617

(22) Filed: Sep. 19, 2001

(65) Prior Publication Data

US 2002/0031550 A1 Mar. 14, 2002

Related U.S. Application Data

(63) Continuation of application No. 09/759,576, filed on Jan. 12, 2001, which is a continuation of application No. 09/254,621, filed as application No. PCT/GB97/02418 on Sep. 8, 1997, now abandoned.

(30) Foreign Application Priority Data

Sep. 12, 1996 (GB) .............................. 9619074

(51) Int. Cl.⁷ ............................ A61K 9/48; A61K 9/20; A61K 9/22; A61K 9/14; A61K 9/16
(52) U.S. Cl. ...................... 424/451; 424/464; 424/468; 424/489; 424/490; 424/472; 424/463
(58) Field of Search ................................ 424/464, 468, 424/472, 451, 489, 490, 463

(56) References Cited

FOREIGN PATENT DOCUMENTS

EP     392 803 A1 *  4/1992

* cited by examiner

*Primary Examiner*—Thurman K. Page
*Assistant Examiner*—Amy E Pulliam
(74) *Attorney, Agent, or Firm*—Linda E. Hall; Stephen Venetianer; Charles M. Kinzig

(57) ABSTRACT

A controlled release formulation of an acetonitrile compound and its use in the treatment and/or prophylaxis of certain disorders.

4 Claims, No Drawings

CONTROLLED RELEASE DOSAGE FORM OF [R-(Z)]-α-(METHOXYIMINO)-α-(1-AZABICYCLO[2.2.2]OCT-3YL) ACETONITRILE MONOHYDROCHLORIDE

This is a continuation of application Ser. No. 09/759,576 filed Jan. 12, 2001 which is a continuation of Ser. No. 09/254,621 filed Mar. 11, 1999 abandoned; which is a 371 of International Application No. PCT/GB97/02418, filed Sep. 8, 1997, which claims priority from GB Application No. 9619074.9, filed Sep. 12, 1996.

The present invention relates to a novel formulation, and to its use in the treatment and/or prophylaxis of certain disorders.

[R-(Z)]-α-(methoxyimino)-α-(1-azabicyclo [2.2.2]oct-3-yl)acetonitrile monohydrochloride (compound X) and methods for its preparation are disclosed in EP-A-0392803, WO95/31456 and WO93/17018. The compound enhances acetylcholine function via an action at muscarinic receptors within the central nervous system. and is therefore of potential use in the treatment and/or prophylaxis of dementia in mammals.

WO96/12486 discloses the use of compound X in the manufacture of a medicament for enhancing amyloid precursor protein processing along a non-amyloidogenic pathway in patients suffering from, or at risk of developing, Alzheimer's disease.

Fast-release swallow tablet and oral solution formulations of compound X both result in rapid absorption of the compound into the circulation, and require twice a day dosing for optimal efficacy.

It has now been surprisingly found that it is possible to formulate compound X, which has very high water solubility and is active at extremely low doses, in such a way that release is controlled to take place over a period of hours. Such a formulation would require dosing only once a day: this is likely to improve compliance in a patient population characterised by poor memory; it may also reduce side-effects in case of accidental overdosing.

Accordingly, the present invention provides a controlled release oral dosage form containing compound X. its parent free base or any other pharmaceutically acceptable salt thereof.

By controlled release is meant any formulation technique wherein release of the active substance from the dosage form is modified to occur at a slower rate than that from an immediate release product, such as a conventional swallow tablet or capsule.

Controlled release includes delayed release wherein release of the active substance from the dosage form is modified to occur at a later time than that from a conventional immediate release product. The subsequent release of active substance from a delayed release formulation may also be controlled to occur at a slower rate.

Examples of controlled release formulations which are suitable for incorporating compound X are described in:

Sustained Release Medications, Chemical Technology Review No. 177. Ed. J. C. Johnson. Noyes Data Corporation 1980.

Controlled Drug Delivery, Fundamentals and Applications. 2nd Edition. Eds. J. R. Robinson, V. H. L Lee. Marcel Dekker Inc. New York 1987.

Such controlled release formulations are preferably formulated in a manner such that release of compound X is effected throughout the gastro-intestinal tract, and takes place predominantly over the first eight to twelve hours following ingestion.

Preferred formulations include wax matrices, swellable and/or gellable polymer or hydrogel matrices. tablets coated with release controlling polymers or waxes, and pellets. granules or beads comprising matrices or coated with release controlling polymers or waxes and then formulated as capsules, compressed tablets or suspensions.

Suitable waxes for matrix formation or release controlling coating include non-ionic beeswax derivatives such as Gelucire 62/05. 50/02 or 50/13 (Gattefosse), glyceryl behenate, other fatty acid mono-, di- or trimesters of glycerol such as Precirol ATO5 (Gattefosse), microcrystalline wax, hydrogenated castor oil or hydrogenated vegetable oil, long-chain aliphatic alcohols such as stearyl alcohol and carnuba wax.

Suitable materials for the formation of hydrogel matrices or swellable and/or gellable polymer matrices may be selected from alkyl celluloses. hydroxyalkylcelluloses, polyvinyl alcohol, polymethacrylates, polymethylmethacrylates, methacrylate/divinylbenzene copolymers, carboxymethylamide, polyoxyalkylene glycols. polyvinyl pyrrolidone and carboxymethyl cellulose. The swellable polymeric material in particular may be selected from crosslinked sodium carboxymethylcellulose, crosslinked hydroxypropylcellulose, high molecular weight polyhydroxypropylmethylcellulose, carboxymethylamide, potassium methacrylate/divinylbenzene copolymer, polymethyimethacrylate, crosslinked polyvinylpyrrolidone and high molecular weight polyvinyl alcohol. The gellable polymeric material in particular may be selected from methylcellulose carboxymethylcellulose, low-molecular weight hydroxypropylmethylcellulose, low-molecular weight polyvinylalcohols, polyoxyethyleneglycols and non-crosslinked polyvinylpyrrolidone. The swellable and gellable polymeric material in particular may be selected from medium-viscosity hydroxypropylmethylcellulose and medium-viscosity polyvinylalcohols.

Release controlling polymers include hydrogel polymers such as those listed above, hydrophobic polymers and enteric, or pH dependent, polymers.

Suitable materials for the formation of hydrophobic release controlling polymer coatings include alkyl celluloses, which may be used in the form of latex suspensions such as Surelease (Colorcon) or Aquacoat (FMC), and methacrylic acid derivatives, which may be used in the form of latex suspensions such as Eudragit RS, RL and NE (Rohm).

Suitable materials for the formation of enteric or pH dependent polymer coatings include methacrylic acid derivatives, which may be used in the form of latex suspensions such as Eudragit L and S (Rohm).

Seal coats, film layers used to separate the various functional layers of the formulation or to provide a final layer to the outside of the formulation, contain suitable materials for film forming such as alkylcelluloses, which may be used in the form of latex suspensions such as Surelease (Colorcon) or Aquacoat (FMC), and hydroxyalkycelluloses such as hydroxypropylmethylcellulose (for example Opadry (Colorcon)).

The formulation may also include plasticisers such as triethyl citrate, dibutyl sebacate or medium chain triglycerides in the release controlling polymer layer.

Pellet-forming materials include suitable grades of microcrystalline cellulose such as Avicel PH101 (FMC).

Granules may be formed from any of the commonly used pharmaceutical fillers or diluents such as lactose, lactose monohydrate, mannitol, microcrystalline cellulose, dicalcium phosphate or search.

Beads may be formed by layering or spraying on non-pareil seeds.

Other suitable ingredients in controlled-release dosage forms include polyethylene glycol and propylene glycol and these, as well as the pharmaceutical fillers, may be used to modify the release rate by inclusion in matrices, pellets, granules or beads.

The formulation may also include hydrophobic excipients that retard the release from the formulation such as ethylcellulose, talc, colloidal silicon dioxide or glyceryl monostearate and/or one or more binders such as hydroxypropylmethylcellulose, microcrystalline cellulose or polyvinylpyrrolidone.

Wetting agents such as sodium lauryl sulphate, lubricants such as magnesium stearate and glidants such as colloidal silica may also be included.

A particularly preferred formulation comprises drug-layered beads coated with a release controlling polymer either alone or in combination with drug-layered beads not coated with a release controlling polymer (immediate release beads). In the drug layering process onto non-pareil beads, appropriate size non-pareil sugar beads may be layered with a solution or dispersion containing the active substance, inert excipients, and/or retardants such as ethylcellulose, talc, colloidal silicon dioxide or glyceryl monostearate and/or one or more binders such as hydroxypropylmethylcellulose or polyvinylpyrrolidone. The layering of the active substance may be accomplished at a predetermined rate and temperature using either a coating pan or a fluid bed drier. The layered beads may be seal coated with a suitable film forming polymer such as hydroxypropylmethylcellulose (e.g. Opadry) or Eudragit® L30D-55 (a methacrylic acid copolymer) and then may be coated with one or more suitable release controlling polymers preferably selected from from alkyl celluloses, hydroxyalkylcelluloses, sodium carboxymethyl cellulose and methacrylic acid derivatives, such as ethylcellulose, Eudragit® RS, Eudragit® RL or Methocel E4M, to produce beads that release compound X over an eight to twelve hour period and/or release compound X in one or more pulses. Seal coated beads may be used for an immediate release dose. The controlled release or a mixture of controlled release and immediate release beads may then be filled into an appropriate size capsule or compressed with inert excipients into tablets of appropriate physical parameters such as shape. size. hardness and disintegration. The polymer(s), release controlling plus any seal coat polymer(s), preferably make up 10 to 30% by weight of the total dosage form. Plasticizer is normally present and may make up at least 2% by weight. Binder(s) and retardant(s) typically make up to 3–10% by weight.

Another particularly preferred formulation comprises a swellable and/or gellable polymer matrix tablet. The polymer matrix is preferably a hydrogel polymer selected from alkyl celluloses such as methylcellulose, hydroxyalkylcelluloses such as hydroxypropylcellulose and hydroxypropylmethylcellulose, polyvinyl alcohol, polymethacrylates, cross-linked polyvinylpyrrolidone and sodium carboxymethyl cellulose. The polymers typically make up 10 to 50% by weight of the tablet. The matrix tablet can be sealed with a hydrophobic release controlling polymer coating such as ethylcellulose (Surelease (Colorcon)) to retard the hydration of the hydrogel matrix in the tablet. The hydrophobic coatings polymer typically make up 4 to 10% by weight of the tablet.

Such matrix tablet formulations can be prepared by either direct compression or wet granulation processes. Coating may be accomplished using a coating pan.

Other preferred formulations are described in U.S. Pat. No. 5,422,123.

Thus, a particular aspect of the invention provides a system for the controlled release of an active substance which is compound X, its parent free base or any other pharmaceutically acceptable salt thereof. comprising (a) a deposit-core comprising an effective amount of the active substance and having defined Geometric form, and (b) a support-platform applied to said deposit-core, wherein said deposit-core contains at leas the active substance, and at least one member selected from the group consisting of (1) a polymeric material which swells on contact with water or aqueous liquids and a gellable polymeric material wherein the ratio of the said swellable polymeric material to said gellable polymeric material is in the range 1:9 to 9:1, and (2) a single polymeric material having both swelling and gelling properties, and wherein the support-platform is an elastic support, applied to said deposit-core so that it partially covers the surface of the deposit-core and follows chances due to hydration of the deposit-core and is slowly soluble and/or slowly gellable in aqueous fluids.

The swellable polymeric material in (1) may be selected from crosslinked sodium carboxymethylcellulose, crosslinked hydroxypropylcellulose, high molecular weight polyhydroxypropyl-methylcellulose, carboxy-methyl starch, potassium methacrylate/divinylbenzene copolymer, crosslinked polyvinylpyrrolidone and polyvinyl alcohol. The gellable polymeric material in (1) may be selected from methylcellulose and non-cross-linked polyvinylpyrrolidone.

The support-platformn may comprise; polymers such as polyhydroxypropylmethylcellulose, polyvinyl alcohol, polyacrylate, polymethacrylate, polyhydroxpropyl cellulose and polysodium carboxymethylcellulose; plasticizers such as polyoxyethylene glycols, castor oil, hydrogenated castor oil, ethyl phthalate, butyl phthalate, natural glycerides, synthetic glycerides and semisynthetic glycerides; binders such as polyvinylpyrrolidone, methylcellulose, ethyl cellulose gum arabic and alginic acid; hydrophilic agents such as mannitol, lactose, starch and colloidal silica, and/or hydrophobic agents such as hydrogenated castor oil, magnesium stearate, a fatly substance, wax, natural glycerides and synthetic glycerides. The polymer(s) typically make up 30 to 90% by weight of the support-platform, for example about 35 to 40%. Plasticizer may make up at least 2% by weight of the support-platform, for example about 15 to 20%. Binder(s), hydrophilic agent(s) and hydrophobic agent(s) typically total up to about 50% by weight of the support-platform, for example about 40 to 50%.

Such formulation may be prepared as generally described in U.S. Pat. No. 5,422,123.

U.S. Pat. No. 4,839,177 discloses a further alternative controlled release formulations suitable for use in the present invention.

Thus a further aspect of the invention provides a system for the controlled-rate release of compound X, consisting of:
a) a deposit-core comprising effective amounts of compound X and having defined geometric form, b) a support-platform applied to said deposit-core wherein said deposit-core contains, mixed with the active substance, at least one member selected from the group consisting of a (a) 5–80% by weight of the total weight of deposit-core of a polymeric material having a high degree of swelling on contact with avatar or aqueous liquids and 90–10% by weight of the total weight of the deposit core of a gellable polymeric material, and (b) a single polymeric material having both swelling and gelling properties, and other adjuvants able to provide the mixture with suitable characteristics for compression and for intake of water, and wherein said support-platform consists of a polymeric material insoluble in aqueous liquids and partially coating said deposit core.

The swellable polymeric material in (a) may be selected from crosslinked sodium carboxymethylcellulose, crosslinked hydroxypropylcellulose, high molecular weight polyhydroxypropyl-methylcellulose, carboxy-methyiamide, potassium methacrylate/divinylbenzene copolymer, polymethylmethacrylate, crosslinked polyvinylpyrrolidone and high molecular weight polyvinyl alcohol. The gellable polymeric material in (a) may be selected from methylcellulose, carboxymethylcellulose, low-molecular weight hydroxypropylmethylcellulose, low-molecular weight polyvinylalcohols, polyoxyethyleneglycols and non-cross-linked polyvinylpyrrolidone. The swellable and gellable polymeric material in (b) may be selected from medium-viscosity hydroxypropylmethylcellulose and medium-viscosity polyvinylalcohols, The support platform may comprise insoluble polymeric material selected from acrylates, cellulose, ethylcellulose, cellulose acetate-propionate, polyethylene, methacrylates. acrylic acid copolymers and high-molecular weight polyvinyvalcohols.

Such formulation may be prepared as generally described in U.S. Pat. No. 4,839,177.

WO 94/06416 discloses a yet further alternative controlled release formulations suitable for use in the present invention.

Thus a yet further aspect of the invention provides a system for the controlled-rate release of compound X, consisting of a pharmaceutical compressed tablet capable of releasing compound X at different rates, consisting of three layers, wherein a first layer contains compound X with immediate or controlled release formulation, composed of rapidly swelling and/or soluble and/or erodible polymeric substances by contact with aqueous fluids, and adjuvants;

a second layer contains compound X, either equal to or different from those of the first layer, with slow release formulation, composed of swelling and/or gellable and/or erodible polymeric substances by contact with aqueous fluids, and adjuvants;

a low-permeability barrier-type layer coating said second layer or, alternatively, placed between the first and second layer, consisting of polymeric substances, adjuvants, plasticizing agents and, if necessary, compound X.

The polymeric substances of the first layer may be selected from cross-linked polyvinylpyrrolidone, low- and medium-molecular-weight hydroxypropyl cellulose and hydroxypropyl methylcellulose, cross-linked sodium carboxymethylcellulose, carboxymethyl starch, potassium methacrylate-divinylbenzene copolymer, polyvinyl alcohols, starches, starch derivatives, microcrystalline cellulose and cellulose derivatives, β-cyclodextrin and dextrin derivatives.

The polymeric substances of the second layer may be selected from the group consisting of hydroxypropyl methylcellulose having molecular weight from 1,000 to 4,000,000, hydroxypropyl cellulose having molecular weight from 2,000 to 2,000,000, carboxyvinyl polymers, polyvinyl alcohols, glucans, scierozlucans, mannans, xanthans. alzinic acid and derivatives thereof, carboxymethylcellulose and derivatives thereof, poly(methyl vinyl ethers/maleic anhydride), ethylcellulose, methylcellulose, and cellulose derivatives.

The adjuvants of the first and second layers may be selected from the group consisting of starch, pregelled starch, calcium phosphate mannitol, lactose, saccharose, glucose, sorbitol, microcrystalline cellulose, gelatin, polyvinylpyrrolidone. methylcellulose, starch solution, ethylcellulose, arabic gum, tragacanth gum, magnesium stearate, stearic acid, colloidal silica, glyceryl monostearate, hydrogenated castor oil, waxes, and mono-, bi-, and trisubstituted glycerides.

The polymeric substances of the barrier type layer may be selected from the group consisting of hydroxypropyl methylcellulose having molecular weight from 1,000 to 4,000,000, hydroxypropyl cellulose having molecular weight from 2,000 to 2,000,000, carboxyvinyl polymers, polyvinyl alcohols, glucans, scleroglucans, mannans, xanthans. carboxymethylcellulose, ethylcellulose, and methylcellulose.

The adjuvants of the barrier-type layer may be selected from the group consisting of glyceryl monostearate, semi-synthetic glycerides, glyceryl palmitostearate, glyceryl behenate, polyvinylpyrrolidone, gelatine, ethylcellulose, methylcellulose, sodium carboxymethylcellulose, magnesium stearate, stearic acid, sodium stearate, talc, sodium benzoate, boric acid, and colloidal silica.

The plasticizing agents of the barrier-type layer may be selected from the group consisting of hydrogenated castor oil, fatty acids, substituted triglycerides and glycerides, polyoxyethylene glycols and derivatives thereof having molecular weight from 400 to 60,000.

Such formulation may be prepared as generally described in WO 94/06416.

The dosage form preferably contains compound X itself.

Compound X has active doses around 5–125 microgramme ($\mu$g) (calculated as free base). It has been found through administration to human patients that efficacy as a cognition enhancer may be obtained at daily doses below 0.01 mg/kg more particularly 0.003 mg/kg and below, for example 0.0001–0.003 mg/kg, such as 0.00035–0.003 mg/kg. 0.0007–0.003 mg/kg, 0.0001–0.0007 mg/kg or 0.00035–0.002 mg/kg.

Suitable unit doses to achieve such daily doses are 5, 12.5, 25.50 or 75$\mu$g, administered twice daily or 50 $\mu$g or 100$\mu$g, once daily. Such unit doses are calculated on the basis of 50–70 kg individuals and as free base.

Suitably, the in vitro release profile of the dosage form i.e. the amount of compound X released over time will be selected so that it will provide an area under the in vivo plasma profile curve that is similar to that obtained following conventional oral administration of a fast release tablet, 5 to 75 $\mu$g (calculated as free base) compound X twice a day. Preferably 25–70% is released over 4 hours and 70–100% is released over 8 hours.

The dosage form of the invention may be used in the treatment and/or prophylaxis of dementia, including Alzheimer's disease, in mammals, and for enhancing amyloid precursor protein processing along a non-amyloidogenic pathway in patients suffering from, or at risk of developing, Alzheimer's disease. These disorders are herein after referred to as "the Disorders".

The present invention provides a method of treating "the Disorders" by administering an effective amount of a controlled release oral dosage form containing compound X, its parent free base or any other pharmaceutically acceptable salt thereof, to a sufferer in need thereof.

The present invention further provides the use of a controlled release oral dosage form containing compound X, its parent free base or any other pharmaceutically acceptable salt thereof, in the manufacture of a medicament for treating "the Disorders".

The present invention also provides a pharmaceutical composition for use in the treatment of "the disorders" which comprises a controlled release oral dosage form containing compound X, its parent free base or any other pharmaceutically acceptable salt thereof.

The following examples illustrate the present invention.

EXAMPLES

In the following examples, the weight shown is the weight of free base, compound X is the hydrochloride salt. (pfb= pure free base). Mesh sizes are US standard.

Example 1 (Wax Matrix)

| Compound X | 0.005–0.1 mg pfb |
|---|---|
| Gelucire 62/05 (Gattefosse) | 190 mg |
| Propylene glycol | 10 mg |

Example 2 (Film Coated Pellets)

| Component | mg/capsule (500 mg) | Function |
|---|---|---|
| Compound X | 0.005–0.1 mg pfb | Active |
| Lactose | 300 | Hydrophilic diluent |
| Avicel PH 101 (FMC) | 200 | Inert pellet matrix |
| Film coat: | w/w of pellet cores | |
| Surelease (Colorcon) | 2–10% | Release controlling polymer coat |
| Silicone antifoam | | Antifoaming agent |

Example 3 (Film Coated Pellets)

| Component | mg/capsule (500 mg) | Function |
|---|---|---|
| Compound X | 0.005–0.1 mg pfb | Active |
| Lactose | 400 | Hydrophilic diluent |
| Avicel PH 101 | 100 | Inert pellet matrix |
| Film coat: | w/w of pellet cores | |
| Aquacoat (FMC) | 2–10% | Release controlling polymer coat |
| Silicone antifoam | | Antifoaming agent |
| Di-butylsebacate | 20–30% (of polymer weight) | Plasticizer |

In Examples 2 and 3, pellets are produced by extrusion/spheronization, using water as a granulation liquid and an appropriate size fraction is obtained by screening. Pellets are then coated in a fluid bed coater (bottom spray) with 2–10% (w/w) of an aqueous Surelease dispersion (15% solids in dispersion).

Desired release profiles are obtained by mixing uncoated (=immediate release pellets) and coated pellets of suitable coating levels (=sustained release pellets), that are then filled into hard gelatine capsules.

Example 4 (matrix pellets)

| Component | mg/capsule (500 mg) | Function |
|---|---|---|
| Compound X | 0.005–0.1 mg pfb | Active |
| Glyceryl behenate | 200 | Hydrophobic matrix |
| Avicel PH 101 | 300 | Inert pellet matrix |
| Sodium lauryl sulphate | 0.1 | Wetting agent |

Pellets are produced by extrusion/spheronization using water and sodium laurylsulphate as a granulation liquid, and an appropriate size fraction is obtained by screening. Pellets may additionally be coated in a fluid bed coater (bottom spray) with aqueous polymer dispersions to further reduce release rates and obtain the desired release profiles.

Example 5 (He Drogel Matrix)

| Excipient | % w/w | mg/tablet | mg/tablet |
|---|---|---|---|
| Compound X | 0.003–0.07 pfb | 0.005 pfb | 0.1 pfb |
| Hydroxypropylcellulose | 25 | 37.5 | 37.5 |
| Purified water | — | — | — |
| Starch | to 100 | 109.5 | 108.5 |
| Magnesium stearate | 2 | 3.0 | 3.0 |
| Total | 100 | 150 | 150 |

Tablets may be prepared by the following procedure:
1. Blend the starch and HPC in a high shear mixer
2. Dissolve the drug into a small quantity of water and spray into blend while mixing
3. Wash spray mechanism with small volume of water into blend while mixing
4. Granulate mix with sufficient water to achieve a medium to heavy granule
5. Partially dry granule
6. Screen through a suitable mill
7. Complete drying of milled granule
8. Lubricate with Mg stearate
9. Compress into tablets with a target weight of 510 mg

Example 6 (Wax Matrix)

| Excipient | % w/w | mg/tablet | mg/tablet |
|---|---|---|---|
| Compound X | 0.003 to 0.07 pfb | 0.005 pfb | 0.1 pfb |
| Lactose Anhydrous | to 100 | to 150 | to 150 |
| Gelucire 62/05 | 18 | 27.0 | 27.0 |
| Magnesium stearate | 2 | 3.0 | 3.0 |
| Total | 100 | 150 | 150 |

Tablets may be prepared by the following procedure:
1. Preblend the drug with a small quantity of lactose
2. Sandwich the drug preblend with the remaining lactose and the required % of Gelucire 62/05 in a preheated pelletiser.
3. Pelletise until the required pellet size has been achieved
4. Remove the pellets and allow them to cool
5. Screen pellets as necessary 6. Lubricate pellets
7. Compress or encapsulate pellets

Example 7 (Controlled Release Bilayer Tablet)

Active Layer

| Component | mg/tablet | Function |
|---|---|---|
| Compound X | 0.005–0.1 mg pfb | Active |
| Hydroxypropylmethylcellulose | 68.5 | Hydrogel matrix former |
| Mannitol | 20 | Soluble filler |
| Ethyl cellulose (applied in ethanolic solution) | 7.5 | Binder |
| Magnesium stearate | 2 | Lubricant |
| Colloidol silica | 2 | Glidant |

Support Platform

| Component | mg/tablet | Function |
|---|---|---|
| Hydroxypropylmethylcellulose | 39.75 | Hydrogel matrix former |
| Hydrogenated castor oil | 6.5 | Insoluble filler |
| Ethylcellulose (applied in ethanolic solution) | 2.5 | Binder |
| Yellow iron oxide pigment | 0.5 | Pigment |
| Magnesium stearate | 0.5 | Lubricant |
| Colloidal silica | 0.25 | Glidant |

Tablets may be prepared as described in U.S. Pat. No. 5433123.

Example 8 (Wax Matrix)

| Component | % w/w | Function |
|---|---|---|
| Compound X | 0.02 pfb | Active |
| Gelucire 50/02 | 91.5 | Wax matrix |
| Gelucire 50/13 | 5 | Wax matrix |
| Propylene glycol | 1.98 | Solvent |
| Colloidal silica | 1.5 | Hydrophobic excipient |
| Sodium dihydrogen citrate | 0–1.5 | Stabilizer |

Process:

The Gelucire waxes were melted together at around 60 degrees C. Compound X was dissolved in propylene glycol, and blended into the waxes. The colloidal silica was then also blended in, and the mixture filled into size 3 hard gelatin capsule shells.

TABLE 1

Release Profile of wax-filled capsules of Compound X in water (0% citrate)

| Time (hr) | % Released |
|---|---|
| 1 | 13 |
| 3 | 29 |
| 5 | 53 |
| 8 | 73 |

Example 9 (Ethylcellulose Coated Beads)

200 mg of non-pariel sugar beads of 16–20, 20–25 or 25–30 mesh size may be used. A medicated layer solution of the following composition was used:

| Component | % w/w | Function |
|---|---|---|
| Compound X | 0.003–0.05 pfb | Active |
| Opadry ® Clear | 3 | Binder |
| Sodium dihydrogen citrate | 1.5 | Stabilizer |
| Purified water | q.s. | |
| Total | 100 | |

Seal coating solution: A solution of Opadry® Clear (YS-1-9025A) in purified water at medicated layer solutions was made by dissolving 100 grams of Opadry® Clear into 900 grams of purified water.

Polymer Coating: A polymer coating dispersion containing ethylcellulose (Surelease ®) of the following composition was made and used for polymer coating the seal coated beads at an 10% to 25% weight gain, in particular 10, 12, 15, 17, 22 and 25%.

| Component | % w/w | Function |
|---|---|---|
| Surelease ® | 60 (25% as solids) | Release controlling polymer coat with plasticiser |
| Purified water | q.s. | |
| Total | 100 | |

Drug layered beads were produced by layering the drug solution onto 25–30 mesh non-pareil beads using a Niro STREA-1 fluid bed dryer so as to layer 100 micrograms of the drug as the free base onto 200 m, of the non-pareil beads. The drug layered beads were seal coated with Opadry® Clear seal coating solution to a weight gain of 3% to produce the immediate release beads. A portion of the immediate release beads were polymer coated to a weight gain of 10% to 25% with the Surelease® coating dispersion. The final polymer coated beads were produced by seal coating the polymer coated beads to a weight gain of 2% with the Opadry® Clear seal coating solution.

TABLE 2

Release Profile Range of Ethylcellulose coated beads, 10–25% by weight of Compound X in Water

| Time (hr) | % Released |
|---|---|
| 1 | 0.8–36 |
| 2 | 5–57 |
| 4 | 13–75 |
| 8 | 18–91 |

Example 10 (Ethylcellulose Coated Beads)

200 mg of non-pareil sugar beads of 16–20, 20–25 or 25–30 mesh size may be used. A medicated layer solution of the following composition was used:

| Component | % w/w | Function |
|---|---|---|
| Compound X | 0.003–0.05 pfb | Active |
| Opadry ® Clear | 3 | Binder |
| Sodium dihydrogen citrate | 1.5 | Stabilizer |
| Purified water | q.s. | |
| Total | 100 | |

Seal coating: A seal coating dispersion containing Eudragit® L30D-55 of the following composition was made and used for seal coating the drug layered beads at an 4% weight gain.

| Component | % w/w | Function |
|---|---|---|
| Eudragit ® L30D-55 | 45 (30% as solids) | Polymeric seal coat |
| Triethyl citrate | 2.02 | Plasticizer |
| Talc | 3.10 | Anti-tack |
| Purified water | q.s. | |
| Total | 100 | |

Polymer Coating: A polymer coating dispersion containing ethylcellulose (Surelease®) of the following composition was made and used for polymer coating the seal coated beads at an 10% to 25% weight gain.

| Component | % w/w | Function |
|---|---|---|
| Surelease ® | 60 (25% as solids) | Release controlling polymer coat with plasticiser |
| Purified water | q.s. | |
| Total | 100 | |

Drug layered beads were produced by layering the drug solution onto 25–30 mesh non-pareil beads using a Niro STREA-1 fluid bed dryer so as to layer 100 micrograms of the drug as the free base onto 200 mg of the non-pareil beads. The drug layered beads were seal coated with Eudragit® L30D-55 seal coating dispersion to a weight gain of 4% to produce the immediate release beads. A portion of the immediate release beads were polymer coated to a weight gain of 10% to 25% with the Surelease® coating dispersion. The final polymer coated beads were produced by seal coating the polymer coated beads to a weight gain of 2% with the Opadry® Clear seal coating solution.

TABLE 3

Release Profile of Eudragit ® L30D Seal Coated/Ethylcellulose Coated Beads of Compound X in Water

| Time (hr) | % Released, 10% Surelease |
|---|---|
| 0.5 | 1.5 |
| 1 | 5 |
| 2 | 20 |
| 4 | 39 |
| 6 | 49 |
| 8 | 56 |

Example 11 (Ethylcellulose Coated Beads)

200 mg of non-pareil sugar beads of 16–20, 20–25 or 25–30 mesh size may be used. A medicated layer solution of the following composition was used:

| Component | % w/w | Function |
|---|---|---|
| Compound X | 0.003–0.05 pfb | Active |
| Opadry ® Clear | 3 | Binder |
| Sodium dihydrogen citrate | 1.5 | Stabilizer |
| Purified water | q.s. | |
| Total | 100 | |

Seal coating solution: A solution of Opadry® Clear (YS-1-9025A) in purified water at 10% solids concentrations was made by dissolving 100 grams of Opadry® Clear into 900 grams of purified water.

Polymer Coating: A polymer coating dispersion containing Ethylcellulose (Aquacoat®) of the following composition was made and used for polymer coating the seal coated beads at 10% weight gain.

| Component | % w/w | Function |
|---|---|---|
| Aquacoat ® | 50 (30% as solids) | Release controlling polymer coat |
| Triethyl Citrate | 2.02 | Plasticizer |
| Purified water | q.s. | |
| Total | 100 | |

Drug layered beads were produced by layering the drug solution onto 25–30 mesh non-pareil beads using a Niro STREA-1 fluid bed dryer so as to layer 100 micrograms of the drug as the free base onto 200 mg of the non-pareil beads. The drug layered beads were seal coated with Opadry® Clear seal coating solution to a weight gain of 3% to produce the immediate release beads. A portion of the immediate release beads were polymer coated to a weight gain of 10% with the Aquacoat® coating dispersion. The final polymer coated beads were produced by seal coating the polymer coated beads to a weight gain of 2% with the Opadry® Clear seal coating solution.

Example 12 (Eudragit Coated Beads)

200 mg of non-pareil sugar beads of 16–20, 20–25 or 25–30 mesh size may be used. A medicated layer solution of the following composition was used:

| Component | % w/w | Function |
|---|---|---|
| Compound X | 0.003–0.05 pfb | Active |
| Opadry ® Clear | 3 | Binder |
| Sodium dihydrogen citrate | 1.5 | Stabilizer |
| Purified water | q.s. | |
| Total | 100 | |

Seal coating solution: A solution of Opadry(® Clear (YS-1-9025A) in purified water at 10% solids concentrations was made by dissolving 100 crams of Opadry® Clear into 900 grams of purified water.

Polymer Coating: A polymer coating dispersion containing Eudragit® RS or RS/RL of the following composition was made and used for polymer coating the seal coated beads at an 10% weight gain.

| Component | % w/w | Function |
| --- | --- | --- |
| Eudragit ® RS 30D | 45 (30% as solids) | Release controlling polymer coat |
| Triethyl citrate | 2.02 | Plasticizer |
| Talc | 3.10 | Anti-tack |
| Purified water | q.s. | |
| Total | 100 | | or

| Component | % w/w | Function |
| --- | --- | --- |
| Eudragit ® RS 30D | 36 (30% as solids) | Release controlling polymer coat |
| Eudragit ® RL 30D | 9 (30% as solids) | Release controlling polymer coat |
| Triethyl citrate | 2.02 | Plasticizer |
| Talc | 3.10 | Anti-tack |
| Purified water | q.s. | |
| Total | 100 | |

Drug layered beads were produced by layering the drug solution onto 25–30 mesh non-pareil beads using a Niro STREA-1 fluid bed dryer so as to layer 100 micrograms of the drug as the free base onto 200 mg of the non-pareil beads. The drug layered beads were seal coated with Opadry® Clear seal coating solution to a weight gain of 3% to produce the immediate release beads. A portion of the immediate release beads were polymer coated to a weight gain of 10% with the Eudragit® RS or RS/RL coating dispersion. The final polymer coated beads can be produced by seal coating the polymer coated beads to a weight gain of 2% with the Opadry® Clear seal coating solution.

TABLE 4

Release Profile of Eudragit ® RS/RL coated beads of Compound X in water

| Time (hr) | % Released |
| --- | --- |
| 0.5 | 0.2 |
| 1 | 0.3 |
| 2 | 0.4 |
| 4 | 1.9 |
| 6 | 13 |
| 8 | 20 |

Example 13 (Methocel Coated Beads)

200 mg of non-pareil sugar beads of 16–20, 20–25 or 25–30 mesh size may be used. A medicated layer solution of the following composition was used:

| Component | % w/w | Function |
| --- | --- | --- |
| Compound X | 0.003–0.05 pfb | Active |
| Methocel E4M | 15 | Release controlling polymer coat |
| Sodium dihydrogen citrate | 1.5 | Stabilizer |
| Purified water | q.s. | |
| Total | 100 | |

Seal coating solution: A solution of Opadry® Clear (YS-1-7006) in purified water at 10% solids concentrations was made by dissolving 100 grams of Opadry® Clear into 900 grams of purified water.

Example 14 (Ethylcellulose Coated Beads with a Retardant)

200 mg of non-pareil sugar beads of 16–20, 20–25 or 25–30 mesh size may be used. A medicated layer solution of the following, composition was used:

| Component | % w/w | Function |
| --- | --- | --- |
| Compound X | 0.003–0.05 pfb | Active |
| Opadry ® Clear | 1.5 | Binder |
| Surelease ® | 1.5 | Retardant |
| Sodium dihydrogen citrate | 1.5 | Stabilizer |
| Purified water | q.s. | |
| Total | 100 | |

Seal coating solution: A solution of Opadry® Clear (YS-1-9025A) in purified water at 10% solids concentrations was made by dissolving 100 grams of Opadry® Clear into 900 grams of purified water.

Polymer Coating: A polymer coating dispersion containing Ethylcellulose (Surelease®) of the following composition was made and used for polymer coating the seal coated beads at 10% weight gain.

| Component | % w/w | Function |
| --- | --- | --- |
| Surelease ® | 60 (25% as solids) | Release controlling polymer coat with plasticiser |
| Purified water | q.s. | |
| Total | 100 | |

Drug layered beads were produced by layering the drug solution onto 25–30 mesh non-pareil beads using a Niro STREA-1 fluid bed dryer so as to layer 100 micrograms of the drug as the free base onto 200 mg of the non-pareil beads. The drug layered beads were seal coated with Opadry® Clear seal coating solution to a weight gain of 3% to produce the immediate release beads. A portion of the immediate release beads were polymer coated to a weight gain of 10% with the Surelease® coating dispersion. The final polymer coated beads can be produced by seal coating the polymer coated beads to a weight gain of 2% with the Opadry® Clear seal coating solution.

TABLE 5

Release Proflie of Ethylcellulose Coated Beads, with Retardant, of Compound X in Water

| | % Released | |
| --- | --- | --- |
| Time (hr) | Without Retardant | With Retardant |
| 0.5 | 12 | 8 |
| 1 | 37 | 22 |
| 2 | 57 | 35 |
| 4 | 73 | 48 |
| 6 | 85 | 53 |
| 8 | | 58 |

Example 15 (Enteric Coated Beads)

200 mg of non-pareil sugar beads of 16–20, 20–25 or 25–30 mesh size may be used. A medicated layer solution of the following composition was used:

| Component | % w/w | Function |
|---|---|---|
| Compound X | 0.003–0.05 pfb | Active |
| Opadry ® Clear | 3 | Binder |
| Sodium dihydrogen citrate | 1.5 | Stabilizer |
| Purified water | q.s. | |
| Total | 100 | |

Seal coated solution: A solution of Opadry® Clear (YS-1-9025A) in purified water at 10% solids concentrations was made by dissolving 100 grams of Opadry® Clear into 900 grams of purified water.

Polymer Coating: A polymer coating dispersion containing Eudragit® L30D-55 of the following composition was made and used for polymer coating the seal coated beads at an 20% weight gain.

| Component | % w/w | Function |
|---|---|---|
| Eudragit L30D-55 | 45.00 (30% as solids) | Enteric (pH dependent) polymer |
| Triethyl citrate | 2.02 | Plasticizer |
| Talc | 3.10 | Anti-tack |
| Purified water | q.s. | |
| Total | 100 | |

Drug layered beads were produced by layering the drug solution onto 25–30 mesh non-pareil beads using a Niro STREA-1 fluid bed dryer so as to layer 100 micrograms of the drug as the free base onto 200 mg of the non-pareil beads. The drug layered beads were seal coated with Opadry® Clear seal coating solution to a weight gain of 3% to produce the immediate release beads. A portion of the immediate release beads were enteric coated to a weight gain of 20% with the Eudragit® enteric coating dispersion. The final enteric coated beads were produced by seal coating the enteric coated beads to a weight gain of 2% with the Opadry Clear seal coating solution.

Example 16 (Matrix Tablet)

| Ingredient | mg/tablet | Function |
|---|---|---|
| Compound X | 0.005–0.1 pfb | Active |
| Hydroxpropyl Methcellulose E4M CR | 75.0 | Hydrogel matrix |
| Sodium Dihydrogen Citrate | 3.00 | Stabilizer |
| Lactose, Fast Flo | 70.38 | Hydrophilic diluent |
| Magnesium Stearate | 1.50 | Lubricant |
| Opadry ® White | 2.25 | Seal coat polymer |

Seal coating solution: A solution of Opadry® Clear (YS-1-9025A) in purified water at 10% solids concentrations was made by dissolving 100 grams of Opadry® Clear into 900 grams of purified water.

Polymer Coating: A polymer coating dispersion containing Ethylcellulose (Surelease®) of the following composition was made and used for polymer coating the seal coated beads at 10% weight gain.

| Component | % w/w | Function |
|---|---|---|
| Surelease ® | 60 (25% as solids) | Release controlling polymer coat with plasticiser |
| Purified water | q.s. | |
| Total | 100 | |

700 grams of core tablets were coated using a Vector LDCS pan to a 3weight gain with the Opadry® Clear seal coating solution. The seal coated tablets were then polymer coated to 4% weight gain using the Surelease®coating dispersion.

TABLE 6

Release Profile for a Matrix Tablet of Compound A in water

| Time (hr) | % Dissolved |
|---|---|
| 1 | 8 |
| 2 | 30 |
| 4 | 58 |
| 8 | 96 |

Example 17 (Controlled Release Bilayer Tablet)

| | Active Layer | |
|---|---|---|
| Component | mg/tablet | Function |
| Compound X | 0.005–0.1 mg pfb | Active |
| Methocel K4M | 15.00 | Hydrogel polymer |
| Lactose monohydrate | 62.0 | Hydrophilic filler |
| Polyvinylpyrrolidone | 3.0 | Binder |
| Magnesium stearate | 1.0 | Hydrophobic lubricant |
| Syloid 244 | 1.0 | Hydrophilic glidant |

| | Support platform | |
|---|---|---|
| Component | mg/tablet | Function |
| Compritol 888 | 15.0 | Plasticizer |
| Lactose monohydrate | 29.0 | Hydrophilic filler |
| Polyvinylpyrrolidone | 4.0 | Binder |
| Magnesium stearate | 1.5 | Hydrophobic lubricant |
| Methocel E5 | 29.4 | Hydrogel polymer |
| Iron oxide | 0.1 | Colourant |

What is claimed is:

1. A controlled release oral dosage form containing [R-(Z)]-α-(methoxyimino)-α-(1-azabicyclo [2.2.2]oct-3-yl) acetonitrile monohydrochloride (compound X) comprising a tablet of the following composition (mg/tablet):

| | |
|---|---|
| Compound X | 0.005–0.1 pfb |
| hydroxymethylcellulose 28–30% methoxyl, 400 mPa s nominal viscosity (2% in water), ultra fine (95% < 100 mesh) | 75.0 |
| Sodium Dihydrogen Citrate | 0–3.00 |
| Lactose | 70.38–73.38 |

| | |
|---|---|
| Magnesium Stearate | 1.50 |
| hydroxypropylmethylcellulose aqueous | 2.25 | dispersion with polyethylene glycol plasticizer seal coated with a solution of hydroxypropylmethylcellulose aqueous dispersion with polyethylene glycol plasticizer in purified water at 10% solids concentrations and polymer coated with a 60% w/w (25% as solids) dispersion containing ethylcellulose latex suspension at 10% weight gain, formed into core tablets, coated with the hydroxypropylmethylcellulose aqueous dispersion with polyethylene glycol plasticizer seal coating solution and polymer coated to 4% weight gain using 60% w/w (25% as solids) dispersion containing ethylcellulose latex suspension.

2. A controlled release oral dosage form containing [R-(Z)]-α-(methoxyimino)-α-(1-azabicyclo [2.2.2]oct-3-yl) acetonitrile monohydrochloride (compound X) in capsule form comprising non-pareil sugar beads of 16–20, 20–25 or 25–30 mesh size, coated to a drug loading of 100 microgrammes (calculated as free base) per 200 mg beads, with a medicated aqueous layer solution of the following composition (% w/w):

| | |
|---|---|
| Compound X | 0.003–0.06 pfb |
| hydroxypropylmethylcellulose aqueous dispersion with polyethylene glycol plasticizer | 3 |
| Sodium dihydride citrate | 0–1.5 | seal coated with a solution of hydroxypropylmethylcellulose aqueous dispersion with polyethylene glycol plasticizer in purified water at 10% solids concentrations to a weight gain of 3%, and a portion of the beads further polymer coated to a weight gain of 10–25% with a 60% w/w (25% as solids) dispersion containing ethylcellulose latex suspension and then seal coated to a weight gain of 2% with the above seal coat.

3. A dosage form containing [R-(Z)]-α-(methoxyimino)-α-(1-azabicyclo [2.2.2]oct-3-yl)acetonitrile monohydrochloride (compound X) comprising a capsule of the following composition (% w/w):

| | |
|---|---|
| Compound X | 0.02 pfb |
| specific mixtures of mono, di and triglycerides | 91.5 | and polyethylene glycol mono and diesters, obtained either by partial alcoholysis of hydrogenated vegetable oils using polyethylene glycol of relative molecular weight ranging 200–2000, or by esterification of saturated fatty acids using polyethylene glycol of relative molecular weight ranging 200–2000, comprising:

free glycerol content: <3%
caprylic acid (C8): <15%
capric acid (C10): <15%
lauric acid (C12): <50%
myristic acid (C14): <25%
palmitic acid (C16): <55%
stearic acid (C18): <97% specific mixtures of monoesters, diesters and triesters of glycerol and monoesters and diesters of macrogols with a mean relative molecular mass between 300 and 4000 comprising:
free glycerol content: <3%
lauric acid (C12): <5%
myristic acid (C14): <5% different nominal amounts of stearic acid (C18) and of palmitic acid (C16), wherein the sum of stearic acid and of palmitic acid is not less than 90%

| | |
|---|---|
| Propylene glycol | 1.98 |
| Colloidal silica | 1.5 |
| Sodium dihydrogen citrate | 0–1.5 | wherein the waxes are melted together and the remaining ingredients blended in and the mixture filled into hard gelatin capsule shells.

4. A dosage form containing [R-(Z)]-α-(methoxyimino)-α-(1-azabicyclo [2.2.2]oct-3-yl)acetonitrile monohydrochloride (compound X) in capsule form comprising non-pareil sugar beads of 16–20, 20–25 or 25–30 mesh size, coated to a drug loading of 100 micrograms (calculated as free base) per 200 mg of beads, with an aqueous medicated layer solution of the following composition (% w/w):

| | |
|---|---|
| Compound X | 0.003–0.05 pfb |
| Hydroxypropylmethylcellulose aqueous dispersion with polyethylene glycol plasticizer | 3 |
| Sodium dihydrogen citrate | 1.5 | seal coated with an aqueous dispersion containing methacrylic acid copolymer of the following composition (% w/w):

| | |
|---|---|
| methyacrylic acid copolymer | 45 (30% as solids) |
| Triethyl citrate | 2.02 |
| Talc | 3.10 |
| at a 4% weight gain | | and a portion of the beads further polymer coated to a weight gain of 10–25% with a 60% w/w (25% as solids) aqueous polymer coating dispersion containing ethylcellulose latex suspension and then seal coated to a weight gain of 2% with the above seal coating solution.

* * * * *